United States Patent [19]

Dieterman et al.

[11] 4,062,824
[45] Dec. 13, 1977

[54] VINYL RESINS CONTAINING EPOXIDIZED MIXED MELLITATE COMPOUNDS

[75] Inventors: Alfred Johannes Dieterman, Mississauga; Roland Hendrick Riem, Oakville, both of Canada

[73] Assignee: Emery Industries, Inc., Cincinnati, Ohio

[21] Appl. No.: 579,091

[22] Filed: May 20, 1975

Related U.S. Application Data

[62] Division of Ser. No. 417,586, Nov. 20, 1973.

[51] Int. Cl.$^2$ ............ C08K 5/12; C08K 5/15; C08K 5/49
[52] U.S. Cl. ............ 260/30.4 R; 260/30.6 R; 260/31.6; 260/31.8 B; 560/76
[58] Field of Search ......... 260/31.8 B, 475 P, 92.8 A, 260/30.4 R, 31.6, 30.6 R

[56] References Cited

U.S. PATENT DOCUMENTS

| 3,351,604 | 11/1967 | Safford et al. | 260/31.8 B |
| 3,872,154 | 3/1975 | Hirzy | 260/31.8 B |
| 3,876,671 | 4/1975 | Turner | 260/31.8 B |

OTHER PUBLICATIONS

Dougherty et al., *SPE Journal*, Nov. 1962, pp. 1387–1394.

*Primary Examiner*—Allan Lieberman
*Attorney, Agent, or Firm*—Gerald A. Baracka; John D. Rice

[57] ABSTRACT

Epoxidized mixed mellitate compounds useful as plasticizers for vinyl polymers such as polyvinyl chloride and which have markedly improved resistance to oils and hydrocarbon extraction have been prepared. The mixed mellitate plasticizers of this invention are trimellitates wherein two of the ester moieties are simple esters derived from monofunctional alcohols with the third ester moiety being a complex ester obtained by the reaction of a diol with an unsaturated monobasic acid subsequently epoxidized at the site of unsaturation.

3 Claims, No Drawings

VINYL RESINS CONTAINING EPOXIDIZED MIXED MELLITATE COMPOUNDS

This is a division of application Ser. No. 417,586, filed Nov. 20, 1973.

BACKGROUND OF THE INVENTION

Numerous plasticizers are used in formulating vinyl plastics, such as polyvinyl chloride. Due to the diversity of end-use applications of these plastic materials, no single plasticizer can provide the necessary balance of physical properties for all end-use applications.

Simple esters based on trimellitic anhydride, such as tri(2-ethylhexyl) trimellitate, are known and have been demonstrated to be effective plasticizers for polyvinyl chloride. Other simple trimellitate esters are described by Paul C. Dougherty et al., in his article entitled "Vinyl Plasticizers from Trimellitic Anhydride" found in Technical Papers, Volume VIII, presented at the Eighteenth Annual Technical Conference of the SPE in January, 1962. Related compounds, such as esters of cyclohexane-1,2,4-tricarboxylic acid and trialkyl esters of trimesic acid, have also been suggested as plasticizers for vinyl chloride polymers in U.S. Pat. Nos. 3,444,237 and 3,043,792, respectively.

In spite of the fact that use of the trimellitate plasticizers has grown at a rapid rate since their introduction, these plasticizers are not without certain disadvantages which limit their use. While the trimellitate plasticizers are generally considered to have satisfactory volatility, good low temperature performance characteristics and low viscosity, they are easily extracted by hydrocarbons such as hexane and oils. The inability of the trimellitate plasticizers to withstand hydrocarbon extraction precludes their use in automotive applications, such as ignition wiring insulation, where ordinarily these plasticizers would be extremely useful due to their ability to be readily compounded with polyvinyl chloride and the otherwise desirable properties they give to the extrudate.

It would be desirable and advantageous if trimellitate plasticizers having enhanced resistivity to hydrocarbon extraction were available. It would be even more advantageous if these improved trimellitate plasticizers could be easily prepared and were relatively low cost materials.

SUMMARY OF THE INVENTION

We have now discovered that trimellitate plasticizers having improved resistance to hydrocarbon extraction are possible by the preparation of certain epoxidized mixed mellitate esters. The mixed mellitates of this invention are derived from trimellitic anhydride and/or trimellitic acid and contain two ester moieties derived from monofunctional alcohols containing from 1 to 22 carbon atoms and a third complex ester moiety obtained by the reaction of a diol containing 2 to 8 caron atoms and an unsaturated monobasic acid containing 4 to 22 carbon atoms which is subsequently epoxidized at the site of the unsaturation. The mixed mellitate plasticizers of this invention have improved resistance to hydrocarbon extraction without sacrificing any of the other desirable properties common to trimellitates such as low volatility, low temperature performance and low viscosity. The mixed mellitates may be employed with a variety of vinyl polymers but are especially for use with polyvinyl chloride homopolymers and copolymers. In general the amount of plasticizer employed will range from about 5 to about 100 parts by weight per 100 parts by weight of the vinyl polymer.

DETAILED DESCRIPTION

The present invention relates to a composition of matter having the formula:

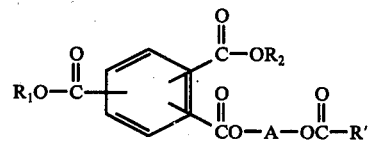

wherein $R_1$ and $R_2$ are hydrocarbon radicals, either the same or different, containing from 1 to 22 carbon atoms; A is a bivalent branched or straight-chain hydrocarbon radical containing from 2 to 8 carbon atoms; and R' is a branched or straight-chain epoxyalkyl radical containing 3 to 21 carbon atoms. The invention also relates to compositions of vinyl polymers containing plasticizing amounts of the aforementioned epoxidized mixed mellitates.

The present compounds are preferably mixed esters of trimellitic acid or trimellitic anhydride and have two ester groups adjacent on the aromatic nucleus. While mixed esters obtained from trimesic acid and hemimellitic acid or anhydride are useful, the preferred plasticizer compounds correspond to the formula

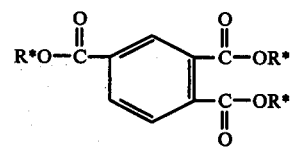

wherein R* represents the groups $R_1$, $R_2$ and

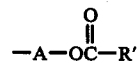

as defined above. It will be observed that the mixed mellitates of the present invention do not contain a single molecular species but, in fact, will consist of a mixture of three different isomers when trimellitic acid or anhydride is employed. This is a consequence of the method of preparing the compounds and in no way affects the effectiveness of the resulting plasticizer compositions. Any of the possible isomers are effective plasticizers in accordance with the terms of this invention and may be employed singularly or as a mixture with one or both of the other isomeric forms. The mixtures may also contain up to about 10% by weight of by-products arising from transesterification reactions during synthesis.

In a preferred form of this invention $R_1$ and $R_2$ of the simple ester groups are hydrocarbon radicals containing from 4 to 18 carbon atoms and more preferably are $C_6$ to $C_{12}$ alkyl radicals. Excellent plasticizers are obtained when $R_1$ and $R_2$ are octyl radicals such as derived from octanol, isooctanol or 2-ethylhexanol. In the preferred embodiment the

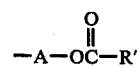

radical comprising the complex ester group is more specifically represented by the formula

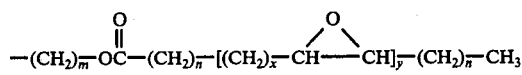

wherein $m$ is an integer from 2 to 6, $n$ is an integer from 0 to 10, $x$ is an integer from 0 to 10, $y$ is an integer from 1 to 3 and the total number of carbon atoms present in the groups is from 8 to 26. For example, when the complex ester group

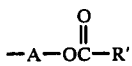

is derived from 1,2-propanediol and epoxidized oleic acid it would have the formula

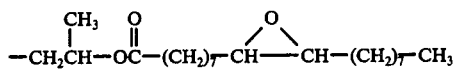

Especially useful compounds are derived from ethylene glycol, 1,2- or 1,3-propanediol and 1,3-, 1,4- and 2,3-butanediol, i.e. where $m$ is equal to 2, 3 or 4, respectively, and epoxidized oleic or linoleic acid, i.e. $C_{18}$ acids containing 1 or 2 epoxidized unsaturated groups. Tall oil fatty acids which are comprised primarily of oleic acid and linoleic acid may be advantageously utilized. Rosin acids should not exceed 5% of the tall oil fatty acids.

To obtain the mixed mellitate compounds of this invention 1 mol of trimellitic anhydride or trimellitic acid are reacted with 2 mols of the appropriate monofunctional alcohol to obtain the simple diester which is a mixture of three isomeric forms. This reaction is represented by the equation:

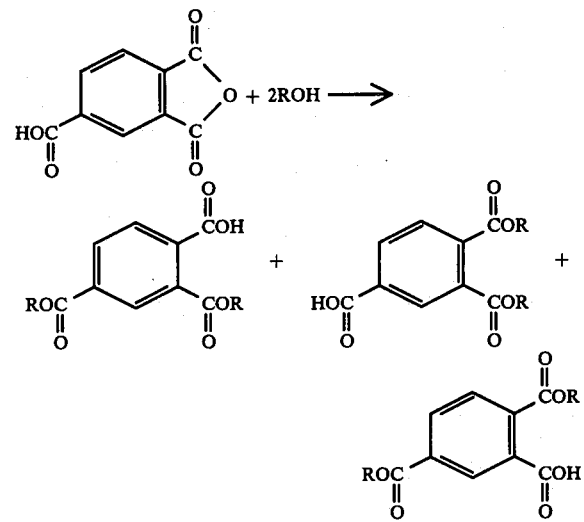

The resulting diester is then reacted with a mol of the diol and this product subsequently reacted with a fatty acid which contains unsaturation and is subsequently epoxidized at the sites of the unsaturation. Suitable catalysts may be employed to facilitate any of the esterification reactions involved. One such catalyst is dibutyl tin oxide. If the mixed mellitates at this stage of the reaction contain unsaturation as a result of the unsaturated acid being employed they are further reacted with a suitable epoxidizing agent in accordance with any of the established techniques known to the art to epoxidize unsaturation. One such technique is to treat the unsaturated trimellitate with hydrogen peroxide in the presence of a suitable catalyst under acidic conditions. Other methods of epoxidation may also be employed with comparable results. The intermediate products formed during any of these reactions such as the diester or any of the subsequent products may be isolated, if desired, or the process may be conducted continuously without isolation by simply adding the next reactant with or without additional catalyst when the prior reaction is complete or essentially complete.

Compounds of this invention find utility in that they are extremely effective plasticizers for vinyl polymers such as polyvinyl chloride homopolymers and copolymers. In addition to having the usual characteristics associated with previously known trimellitate plasticizers such as good volatility, good low temperature performance, and low viscosity, the mixed mellitates also have markedly improved resistance to extraction by hydrocarbons such as hexane and oils. This is extremely important for automotive wire applications where a high degree of resistivity to hydrocarbons is required.

In accordance with the present invention the mixed mellitates are useful for plasticizing vinyl polymers. The term vinyl polymers is intended to encompass both homopolymers and copolymers derived from vinyl monomers, that is, compounds containing the $CH_2=C<$ group. Most commonly the vinyl polymers useful for this invention are prepared by the polymerization of one or more monomers selected from the group consisting of vinyl chloride; vinyl bromide; vinyl acetate; vinylidene chloride; lower allyl esters; vinyl alkyl ethers; and acrylic and methacrylic esters such as ethyl acrylate, methyl acrylate, and methyl methacrylate; acrylic acid and methacrylic acid; acrylonitrile and methacrylonitrile; and the like. Typical copolymer compositions may be obtained by the copolymerization of vinyl chloride with vinyl acetate; vinyl chloride with vinyl butyrate; vinyl chloride with vinyl propionate; vinyl chloride with vinylidene chloride; vinyl chloride with methyl acrylate; vinyl chloride with 2-ethylhexyl acrylate; and vinyl chloride with two or more monomers such as mixtures of vinylidene chloride, and 2-ethylhexyl acrylate; and the like. The plasticizers are also useful for acrylonitrilebutadiene-styrene terpolymers, chloroprene polymers, butadiene-styrene copolymers, butadiene-acrylonitrile copolymers, polystyrene, polyacetals, and the like. Especially useful and effective plasticization is obtained when the present mixed mellitates are employed with polyvinyl chloride homopolymer and copolymers of vinyl chloride with one or more other copolymerizable vinyl monomers.

In general, the amount of plasticizer may range from about 5 to 100 parts by weight per 100 parts by weight of the vinyl polymer. Excellent results are obtained when about 10 to about 70 parts by weight of the mixed mellitate is employed per 100 parts by weight of the polyvinyl chloride homopolymer or copolymer. Such compositions exhibit a high degree of resistivity to extraction with hydrocarbons such as oil and hexane and are especially useful for automotive wire coating applications.

The mixed mellitate plasticizers are incorporated into the vinyl polymers prior to curing, molding or extruding. They may be incorporated by mixing the powdered resin with the liquid plasticizer followed by mixing and/or kneading or they may be mixed on a heated mill. The plasticizer may be added as such, in a masterbatch solution, or the plasticizer may be emulsified and the emulsion added to the polymeric material. In general the plasticized compositions have excellent milling characteristics and require no special processing. The mixed mellitates may be used in conjunction with other primary plasticizers such as dioctyl phthalate, diisooctyl phthalate, dioctyl adipate, trioctyl phosphate, various polymeric plasticizers, epoxides, and the like. They may also be incorporated with other compounding ingredients including antioxidants such as phosphites, amines and phenols; pigments and other colorants; fillers; lubricants; antisticking agents; curing agents; and the like. The mixed mellitate plasticizers and the various compounding ingredients may be prepared as a masterbatch and added to the polymer as such or the various ingredients may be mixed in separately.

EXAMPLE I

Into a glass reactor fitted with a stirrer, thermometer, fractionating column, condenser and nitrogen inlet, are charged 192 grams (1 mol) trimellitic anhydride and 260 grams (2 mols) 2-ethylhexanol. 0.5 grams dibutyl tin oxide was added as a catalyst. The reaction mixture was heated at about 190° C with stirring while maintaining a pressure of about 160 mm absolute on the system. Water was removed from the reaction by a trap attached to the condenser. After about 1 hour the acid number of the product was about 124 (theoretical 129) and the vacuum was released by introduction of nitrogen into the system until atmospheric pressure was established in the reactor. 90 grams (1 mol) 1,3-butanediol and 0.5 grams dibutyl tin oxide were then added and the temperature increased to about 235° C while water of reaction was removed for about 1 hour. The acid value was 1.1, the molecular weight of the product was 520 (theoretical 506) and the hydroxyl value was 107 (theoretical 111). The reaction was continued without isolation of the above intermediates by the introduction of 284 grams (1 mol) tall oil fatty acid and 0.5 grams dibutyl tin oxide and heating at about 235° C with a pressure of about 150 mm absolute on the system. The reaction was continued until the final product has an iodine value of 48.1 (theoretical 49.0).

The tall oil fatty acids had the following typical properties:
FFA: 98.8
Iodine Value: 130
Color (Gardner): 3−
Unsaponifiables: 1.7%
Rosin Acids: 0.9%

EXAMPLE II

The product of Example I was epoxidized as follows: Into a 1-liter glass flask equipped with a stirrer, thermometer, reflux condenser and dropping funnel are charged 528 grams (1 mol unsaturation) of the product of Example I, 20 grams (0.33 mol) glacial acetic acid, 106 grams heptane and 10.6 grams cation exchange resin (Ionac C244 — a product of Ionac Chemical Company). The reaction mixture was heated to about 80° C and 58.3 grams of 70% hydrogen peroxide (1.2 mols) added slowly over 15 minutes. The temperature was then maintained for 2 hours at 80° to 85° C after which time the reaction was terminated by the addition of 200 mls cold water. The resulting oil layer was washed with water until neutral to phenolphthalein. Heptane was distilled off under vacuum with the last traces removed by steam stripping and the product dried and filtered. Properties of the resulting epoxidized mixed mellitate are listed in Table I.

EXAMPLE III

The process of Example I was repeated except that the diol employed was ethylene glycol. The epoxidation was conducted in the manner described in Example II. The resulting mixed mellitate had the specifications listed in Table I.

EXAMPLE IV

55 Parts of the mixed mellitate plasticizer of Example II, 100 parts vinyl chloride (Geon 102 EP-F5 - B. F. Goodrich Chemical Co.), 2 parts Ferro 1820 (a barium-cadmium stabilizer produced by Federal Chemical), 1 part Ferro 903 (a liquid organic inhibitor produced by Federal Chemical) were milled by conventional methods and the plasticized resin evaluated. The physical properties of the composition were as follows:
% Elongation: 300
100% Modulus (PSI): 1650
Tensile (PSI): 2995
Hardness (Ins/10 seconds: 90/82

TABLE I
Properties of Epoxidized Mixed Mellitates

|  | Product of Example II | Product of Example III |
|---|---|---|
| Color (Gardner) | 3− | 3+ |
| Viscosity cps at 25° C | 916 | 1188 |
| Refractive Index $n_D^{25}$ | 1.4858 | 1.4876 |
| Specific Gravity, 25° C | 1.0127 | 1.0226 |
| Pour Point, ° C | −14 | −15 |
| Oxirane Number | 2.6 | 2.4 |
| Acid Value | 0.9 | 2.5 |
| Iodine Value | 2.7 | 2.4 |

The plasticized vinyl composition was then further evaluated for resistance to extraction by immersing samples in a standard white mineral oil (Atreol No. 9) for 24 hours at 50° C. The sample plasticized in accordance with this invention showed only a 1.93 weight percent loss after this period of time. This is a marked improvement over a similar polyvinyl chloride sample plasticized with trioctyltrimellitate which gave a 7.72 percent weight loss when subjected to identical test conditions. Similarly, a sample of the polyvinyl chloride plasticized with the mixed mellitate was extracted in hexane for 24 hours at 50° C and showed an 11.84% weight loss. This is more than a 100% improvement over polyvinyl chloride plasticized with trioctyl trimellitate which gave a 27.58% weight loss in hexane under identical conditions. These results clearly demonstrate that the products of the present invention are excellent primary plasticizers and that they have markedly improved resistivity to oil and hexane extraction compared to known trimellitate plasticizers.

EXAMPLE V

55 Parts of the mixed mellitate plasticizer of Example III were evaluated in a manner identical to Example IV. The physical properties of the composition were as follows:
% Elongation: 275
100% Modulus (PSI): 1975
Tensile (PSI): 3175
Hardness (Ins/10 seconds): 94/89

Oil Extraction (Atreol No. 9, 24 hrs, 50° C): 0.42%
Hexane Extraction: 8.2%

Similar results are observed when epoxidized mixed mellitate plasticizers prepared with commercial oleic acid and linoleic acid are employed for the tall oil fatty acids.

We claim:

1. A plasticized vinyl resin composition having impoved resistance to hydrocarbons comprising 100 parts polyvinyl chloride homopolymer or polyvinyl chloride copolymer and 5 to 100 parts of an epoxidized mixed mellitate of the formula

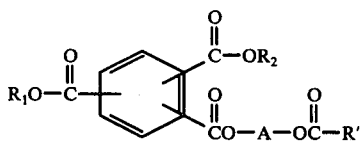

wherein $R_1$ and $R_2$ are alkyl radicals having from 4 to 18 carbon atoms, A is a bivalent hydrocarbon radical having from 2 to 8 carbon atoms and R' is a branched or straight-chain epoxyalkyl radical having from 3 to 21 carbon atoms derived from an unsaturated monobasic acid and epoxidized at the sites of unsaturation.

2. The resin composition of claim 1 wherein the epoxidized mixed mellitate is derived from trimellitic acid or trimellitic anhydride and wherein the radical

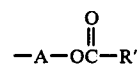

corresponds to the formula

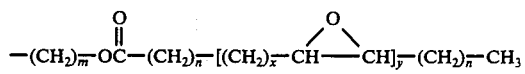

wherein $m$ is an integer from 2 to 6, $n$ and $x$ are integers from 0 to 10, $y$ is an integer from 1 to 3 and the total number of carbon atoms in the group is between 8 and 26.

3. The resin composition of claim 2 which contains 10 to 70 parts epoxidized mixed mellitate per 100 parts polyvinyl chloride resin and wherein A is a bivalent branched or straight-chain hydrocarbon radical derived from a diol selected from the group consisting of ethylene glycol, 1,2-propanediol, 1,3-propanediol, 1,3-butanediol, 1,4-butanediol and 2,3-butanediol and R' is a radical derived from tall oil fatty acids and epoxidized at the sites of unsaturation.

* * * * *